United States Patent

Ogura et al.

Patent Number: 6,022,320
Date of Patent: Feb. 8, 2000

[54] BLOOD PRESSURE MONITOR APPARATUS

[75] Inventors: Toshihiko Ogura, Inuyama; Hidekatsu Inukai, Nagoya, both of Japan

[73] Assignee: Colin Corporation, Komaki, Japan

[21] Appl. No.: 08/867,886

[22] Filed: Jun. 3, 1997

[30] Foreign Application Priority Data

Aug. 1, 1996 [JP] Japan .................................. 8-203839

[51] Int. Cl.$^7$ .................................................. A61B 5/02
[52] U.S. Cl. ........................... 600/490; 600/485; 600/494
[58] Field of Search .................................. 600/490, 491, 600/492, 494, 495, 499, 481, 515

[56] References Cited

U.S. PATENT DOCUMENTS

| | | | |
|---|---|---|---|
| 5,131,391 | 7/1992 | Sakai et al. | 600/490 |
| 5,653,241 | 8/1997 | Harada et al. | 600/490 |
| 5,743,857 | 4/1998 | Shinoda et al. | 600/496 |
| 5,776,071 | 7/1998 | Inukai et al. | 600/493 |
| 5,830,148 | 11/1998 | Inukai et al. | 600/481 |
| 5,830,149 | 11/1998 | Oka et al. | 600/500 |
| 5,853,371 | 12/1998 | Inukai et al. | 600/483 |
| 5,865,756 | 2/1999 | Peel, III | 600/490 |

*Primary Examiner*—Cary O'Connor
*Assistant Examiner*—Navin Natnithithadha
*Attorney, Agent, or Firm*—Oliff & Berridge, PLC

[57] ABSTRACT

A blood pressure (BP) monitor apparatus including a BP measuring device which measures a BP value of a living subject by changing a pressing pressure of a cuff, an estimated blood pressure (EBP) determining device which determines an EBP value of the subject, based on each of successive sets of pulse-wave propagation information (PWPI) of the subject, according to a blood pressure-pulse wave propagation information (BP-PWPI) relationship, a preparing device which prepares a plurality of candidates for the BP-PWPI relationship, a calculating device which calculates a plurality of EBP values, based on each of successive sets of PWPI of the subject, according to the plurality of candidates, and thereby providing a plurality of groups of calculated EBP values which correspond to the plurality of candidates, respectively, a starting device which controls the BP measuring device to measure a BP value of the subject, when at least one of respective changes of the plurality of groups of EBP values exceeds a first reference value, and a selecting device which selects, as the BP-PWPI relationship, one of the plurality of candidates which corresponds to one of the plurality of groups of EBP values which includes the EBP value that is the most approximate to the BP value.

17 Claims, 7 Drawing Sheets

BLOOD PRESSURE MONITOR APPARATUS

BACKGROUND OF THE INVENTION

1. Field of the Invention

The present invention relates to a blood pressure monitor apparatus which monitors a blood pressure of a living subject, based on information on a pulse wave which propagates through an artery of the subject.

2. Related Art Statement

There is known, as information on a pulse wave which propagates through an artery of a living subject, a pulse-wave propagation time DT or a pulse-wave propagation velocity $V_M$ (m/s). The pulse-wave propagation time DT represents a time in which a pulse wave propagates between predetermined two different locations of the subject. Additionally, there is known that the pulse-wave propagation information is, within a predetermined range, substantially proportional to a blood pressure BP (mmHg) of the subject. Therefore, there has been proposed a blood pressure monitor apparatus which determines, in advance, coefficients $\alpha$, $\beta$ in an expression: $EBP=\alpha(DT)+\beta$ (where a is a negative value) or $EBP=\alpha(V_M)+\beta$ (where a is a positive value), based on a measured blood pressure value BP of the subject and an obtained pulse-wave propagation time (DT) or an obtained pulse-wave propagation velocity ($V_M$), determines an estimated blood pressure value EBP of the subject, based on each set of subsequently obtained pulse-wave propagation information, according to the above mentioned expression, and starts a blood pressure measurement using a cuff upon detection of abnormality of the estimated blood pressure value EBP.

In the case where a relationship between blood pressure and pulse-wave propagation information as indicated above is determined, at least two combinations of blood pressure value and pulse-wave propagation information are needed. To accurately determine the relationship between blood pressure and pulse-wave propagation information, it is desirable that a difference between two blood pressure values included in the two combinations of blood pressure value and pulse-wave propagation information be sufficiently large. However, the above blood pressure monitor apparatus cannot accurately determine the relationship between blood pressure and pulse-wave propagation information if a second blood pressure measurement using a cuff which follows a first blood pressure measurement is carried out independent of an actual blood pressure level of the subject. Otherwise, if a blood pressure measurement using a cuff is repeated until a sufficiently large difference between two blood pressure values is obtained, the subject will feel uncomfortable because of the repeated pressing of the cuff.

SUMMARY OF THE INVENTION

It is therefore an object of the present invention to provide a blood pressure monitor apparatus which monitors a blood pressure value of a living subject, based on information on a pulse wave which propagates through an artery of the subject, wherein a relationship between blood pressure and pulse-wave propagation information is accurately and efficiently determined.

The above object has been achieved by the present invention, which provides a blood pressure monitor apparatus comprising: (a) a blood pressure measuring device which includes a cuff and measures an actual blood pressure value of a living subject by changing a pressing pressure of the cuff applied to a body portion of the subject; (b) estimated blood pressure determining means for successively determining an estimated blood pressure value of the subject, based on each of successive sets of actual pulse-wave propagation information of the subject, according to a relationship between blood pressure and pulse-wave propagation information; (c) preparing means for preparing a plurality of candidates for the relationship between blood pressure and pulse-wave propagation information; (d) calculating means for successively calculating a plurality of estimated blood pressure values, based on each of successive sets of actual pulse-wave propagation information of the subject, according to the plurality of candidates prepared by the preparing means, respectively, and thereby providing a plurality of groups of successively calculated estimated blood pressure values which correspond to the plurality of candidates, respectively; (e) starting means for controlling the blood pressure measuring device to measure an actual blood pressure value of the subject, when at least one of respective changes of the plurality of groups of estimated blood pressure values provided by the calculating means exceeds a first reference value; and (f) selecting means for selecting, as the relationship between blood pressure and pulse-wave propagation information, one of the plurality of candidates which corresponds to one of the plurality of groups of estimated blood pressure values which includes the estimated blood pressure value that is most approximate to the actual blood pressure value measured by the blood pressure measuring device under control of the starting means.

In the blood pressure monitor apparatus in accordance with the present invention, the calculating means successively calculates a plurality of estimated blood pressure values, based on each of successive sets of actual pulse-wave propagation information of the subject, according to the plurality of candidates prepared by the preparing means, respectively, and thereby providing a plurality of groups of successively calculated estimated blood pressure values which correspond to the plurality of candidates, respectively. The starting means controls the blood pressure measuring device to measure an actual blood pressure value of the subject, when at least one of respective changes of the plurality of groups of estimated blood pressure values provided by the calculating means exceeds the first reference value. The selecting means selects, as the relationship between blood pressure and pulse-wave propagation information, one of the plurality of candidates which corresponds to one of the plurality of groups of estimated blood pressure values which includes the estimated blood pressure value that is most approximate to the actual blood pressure value measured by the blood pressure measuring device under control of the starting means. Thus, the present blood pressure monitor apparatus carries out a blood pressure measurement using the cuff in response to a sufficiently large change of blood pressure of the subject, and accurately determines the relationship between blood pressure and pulse-wave propagation information with the least number of blood pressure measurements.

According to a preferred feature of the present invention, each of the plurality of candidates comprises the following expression: $EBP=\alpha(PWPI)+\beta$, where EBP is blood pressure, PWPI is pulse-wave propagation information, a is a coefficient and $\beta$ is a constant.

According to another feature of the present invention, the preparing means comprises: (g) coefficient storing means for storing a plurality of predetermined coefficients for the plurality of candidates, respectively; (h) first controlling means for controlling the blood pressure measuring device to measure a first actual blood pressure value of the subject; and (i) constant determining means for determining a plurality of constants for the plurality of candidates, respectively, by substituting the plurality of predetermined coefficients for the respective coefficients of the plurality of candidates and substituting the first blood pressure value and a set of actual pulse-wave propagation information for the blood pressure and the pulse-wave propagation information of each of the candidates. In this case, the blood pressure monitor apparatus can prepare the plurality of candidates with a certain degree of accuracy, for the relationship between blood pressure and pulse-wave propagation information.

According to another feature of the present invention, the starting means comprises: (j) first judging means for judging whether at least one of the respective changes of the plurality of groups of estimated blood pressure values from the first actual blood pressure value exceeds the first reference value; and (k) second controlling means for controlling the blood pressure measuring device to measure a second actual blood pressure value of the subject, when the first judging means makes a positive judgment. In this case, the first reference value is a criterion for finding a sufficiently large blood pressure change of the subject. Thus, the blood pressure monitor apparatus can efficiently carry out a blood pressure measurement using the cuff for determining the relationship between blood pressure and pulse-wave propagation information, after the sufficiently large blood pressure change of the subject is found.

According to another feature of the present invention, the selecting means comprises (l) second judging means for judging whether a change of the second actual blood pressure value from the first actual blood pressure value is greater than a second reference value. When the second judging means makes a negative judgment, the constant determining means determines a plurality of constants for the plurality of candidates, respectively, based on the second blood pressure value, the calculating means successively calculates a plurality of estimated blood pressure values, based on each of successive sets of actual pulse-wave propagation information of the subject, according to the plurality of candidates, respectively, and thereby providing a plurality of groups of successively calculated estimated blood pressure values which correspond to the plurality of candidates, respectively, the first judging means judges whether at least one of the respective changes of the plurality of groups of estimated blood pressure values from the second actual blood pressure value exceeds the first reference value, and the second controlling means controls the blood pressure measuring device to measure a third actual blood pressure value of the subject. When the second judging means makes a positive judgment, the selecting means selects, as the relationship between blood pressure and pulse-wave propagation information, the one of the plurality of candidates which corresponds to one of the plurality of groups of estimated blood pressure values which includes the estimated blood pressure value that is most approximate to the third actual blood pressure value measured by the blood pressure measuring device under control of the second controlling means. In this case, the second reference value may be a value (e.g., 20 mmHg) higher than a blood-pressure change generated in synchronism with a respiration of the subject. Thus, in the blood pressure monitor apparatus, an operation of the selecting means is carried out when the second judging means makes a positive judgment, and accordingly the accuracy of the relationship between blood pressure and pulse-wave propagation information is raised.

BRIEF DESCRIPTION OF THE DRAWINGS

The above and optional objects, features, and advantages of the present invention will better be understood by reading the following detailed description of the preferred embodiments of the invention when considered in conjunction with the accompanying drawings, in which.

DETAILED DESCRIPTION OF THE PREFERRED EMBODIMENTS

Figure 1:
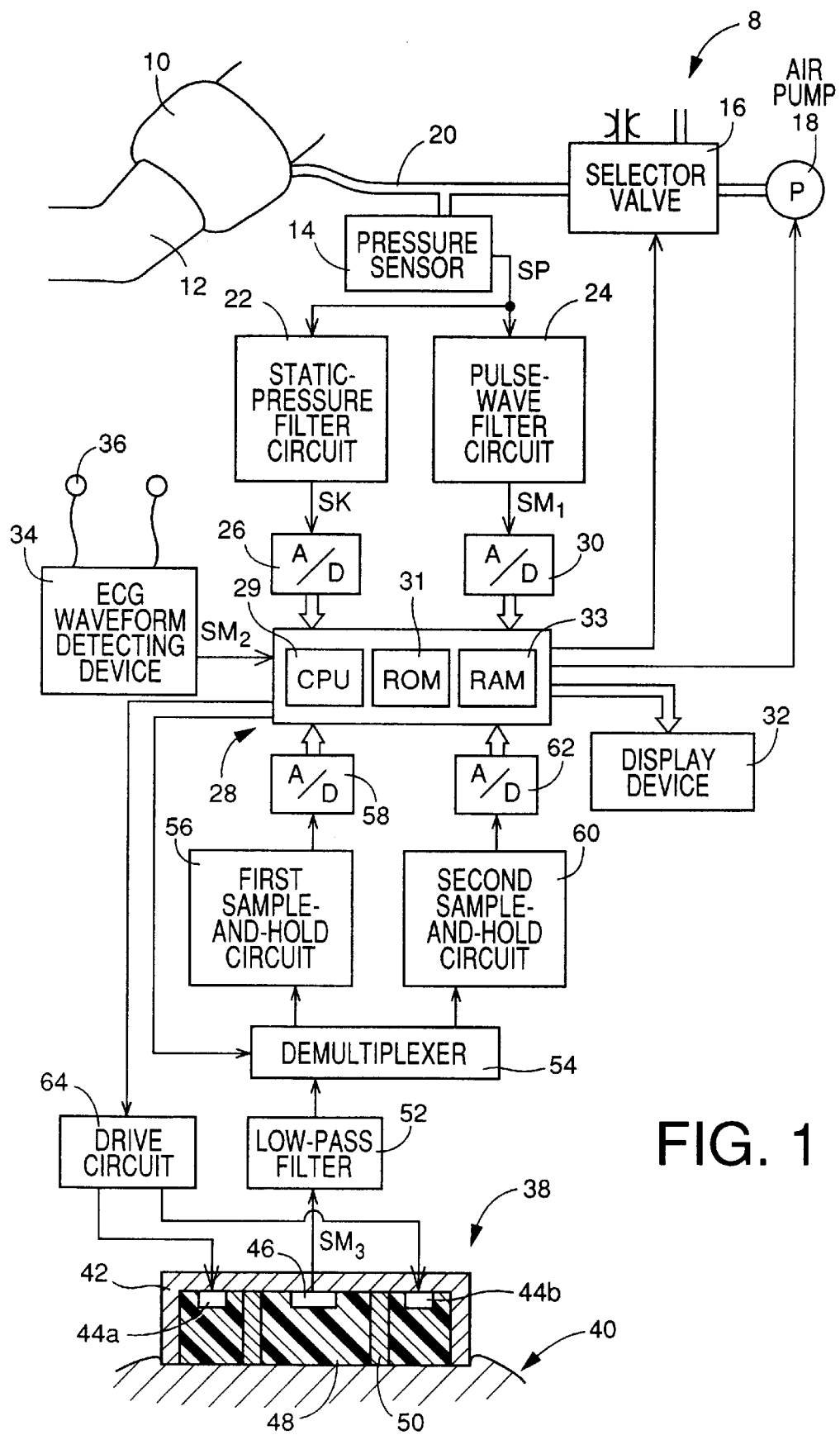
FIG. 1 is a diagrammatic view of a blood pressure monitor apparatus embodying the present invention.

Referring to FIG. 1, there will be described a blood pressure (BP) monitor apparatus 8 embodying the present invention.

In FIG. 1, the BP monitor apparatus 8 includes a cuff 10 which has a belt-like cloth bag and a rubber bag accommodated in the cloth bag and which is adapted to be wound around an upper arm 12 of a patient, for example, a pressure sensor 14, a selector valve 16 and an air pump 18 each of which is connected to the cuff 10 via a piping 20. The selector valve 16 is selectively placed in an inflation position in which the selector valve 16 permits a pressurized air to be supplied to the cuff 10, a slow-deflation position in which the selector valve 16 permits the pressurized air to be slowly discharged from the cuff 10, and a quick-deflation position in which the selector valve 16 permits the pressurized air to be quickly discharged from the cuff 10.

The pressure sensor 14 detects an air pressure in the cuff 10, and supplies a pressure signal SP representative of the detected pressure to each of a static pressure filter circuit 22 and a pulse-wave filter circuit 24. The static pressure filter circuit 22 includes a low-pass filter and extracts, from the pressure signal SP, a static component contained in the signal SP, i.e., cuff pressure signal SK representative of the static cuff pressure. The cuff pressure signal SK is supplied to an electronic control device 28 via an analog-to-digital (A/D) converter 26. The pulse-wave filter circuit 24 includes a band-pass filter and extracts, from the pressure signal SP, an oscillating component having predetermined frequencies, i.e., pulse-wave signal SM The pulse-wave signal $SM_1$ is supplied to the electronic control device 28 via an A/D converter 30. The pulse-wave signal $SM_1$ represents an oscillatory pressure wave which is produced from a brachial artery (not shown) of the patient in synchronism with the heartbeat of the patient and is propagated to the cuff 10.

The electronic control device 28 is provided by a so-called microcomputer including a central processing unit (CPU) 29, a read only memory (ROM) 31, a random access memory (RAM) 33 and an input-and-output (I/O) port (not shown). The CPU 29 processes signals according to control programs pre-stored in the ROM 31 by utilizing a temporary-storage function of the RAM 33, and supplies drive signals to the selector valve 16 and the air pump 18 through the I/O port.

The BP monitor apparatus 8 further includes an electrocardiographic (ECG) waveform detecting device 34 which continuously detects an ECG waveform representative of an action potential of a cardiac muscle of a living subject, through a plurality of electrodes 36 being put on predetermined portions of the subject, and supplies an ECG waveform signal $SM_2$ representative of the detected ECG waveform to the electronic control device 28. The ECG waveform detecting device 34 is used for detecting a Q-wave or a R-wave of the ECG waveform which corresponds to a time point when the output of blood from the heart of the subject toward the aorta of the subject is started. Thus, the ECG waveform detecting device 34 functions as a first pulse wave detecting device.

The BP monitor apparatus 8 still further includes a photoelectric pulse wave detecting probe 38 (hereinafter, referred to as the "probe") which is employed as part of a pulse oximeter. The probe 38 may function as a second pulse wave detecting device or a peripheral pulse wave detecting device for detecting a pulse wave propagated to a peripheral artery including capillaries. The probe 38 is adapted to be set on a skin or a body surface 40 of the subject, e.g., an end portion of a finger of the patient, with the help of a band (not shown) such that the probe 38 closely contacts the body surface 40. The probe 38 includes a container-like housing 42 which opens in a certain direction, a first and a second group of light emitting elements 44a, 44b, such as LEDs (light emitting diodes), which are disposed on an outer peripheral portion of an inner bottom surface of the housing 42 (hereinafter, referred to as the light emitting elements 44 in the case where the first and second group of light emitting elements 44a, 44b need not be discriminated from each other), a light receiving element 46, such as a photodiode or a phototransister, which is disposed on a central portion of the inner bottom surface of the housing 42, a transparent resin 48 which is integrally disposed in the housing 42 to cover the light emitting elements 44 and the light receiving element 46, and an annular shade member 50 which is disposed between the light emitting elements 44 and the light receiving element 46, for preventing the lights emitted toward the body surface 40 by the light emitting elements 44 and reflected from the body surface 40, from being received by the light receiving element 46.

The first and second groups of light emitting elements 44a, 44b emit a red light having about 660 nm wavelength and an infrared light having about 800 nm wavelength, respectively. The first and second light emitting elements 44a, 44b alternately emit the red and infrared lights at a predetermined frequency. The lights emitted toward the body surface 40 by the light emitting elements 44 are reflected from a body tissue of the subject where a dense capillaries occur, and the reflected lights are received by the common light receiving element 46. In place of the 660 nm and 800 nm wavelengths lights, the first and second light emitting elements 44a, 44b may employ various pairs of lights each pair of which have different wavelengths, so long as one light of each pair exhibits significantly different absorption factors with respect to oxygenated hemoglobin and reduced hemoglobin, respectively, and the other light exhibits substantially same absorption factors with respect to the two sorts of hemoglobin, i.e., has a wavelength which is reflected by each of the two sorts of hemoglobin.

The light receiving element 46 outputs, through a low-pass filter 52, a photoelectric pulse-wave signal $SM_3$ representative of an amount of the received light. The light receiving element 46 is connected to the low-pass filter 52 via an amplifier or the like. The low-pass filter 52 eliminates, from the photoelectric pulse-wave signal $SM_3$ input thereto, noise having frequencies higher than that of a pulse wave, and outputs the noise-free signal $SM_3$, to a demultiplexer 54. The photoelectric pulse wave represented by the photoelectric pulse-wave signal $SM_3$ can be said as a volume pulse wave produced in synchronism with a pulse of the patient. That is, the photoelectric pulse wave is a pulse-synchronous wave.

The demultiplexer 54 is alternately switched according to signals supplied thereto from the electronic control device 28 in synchronism with the light emissions of the first and second light emitting elements 44a, 44b. Thus, the demultiplexer 54 successively supplies, to the I/O port (not shown) of the electronic control device 28, an electric signal $SM_R$ representative of the red light through a first sample-and-hold circuit 56 and an A/D converter 58, and an electric signal $SM_{IR}$ representative of the infrared light through a second sample-and-hold circuit 60 and an A/D converter 62. The first and second sample-and-hold circuits 56, 60 hold the electric signals $SM_R$, $SM_{IR}$ input thereto, respectively, and do not output those current signals to the A/D converters 58, 62, before the prior signals $SM_R$, $SM_{IR}$ are completely converted by the two A/D converters 58, 62, respectively.

In the electronic control device 28, the CPU 29 carries out a measuring operation according to control programs pre-stored in the ROM 31 by utilizing a temporary-storage function of the RAM 33. More specifically, the CPU 29 generates a light emit signal SLV to a drive circuit 64 so that the first and second light emitting elements 44a, 44b alternately emit the red and infrared lights at a predetermined frequency, respectively, such that each light emission lasts for a predetermined period. In synchronism with the alternate light emissions by the first and second light emitting elements 44a, 44b, the CPU 29 generates a switch signal SC to the demultiplexer 54 so as to correspondingly place the demultiplexer 54 in a first or a second position. Thus, the signals $SM_R$, $SM_{IR}$ are separated from each other by the demultiplexer 54 such that the signal $SM_R$ is supplied to the first sample-and-hold circuit 56 while the signal $SM_{IR}$ is supplied to the second sample-and-hold circuit 60. Further, the CPU 29 determines an oxygen saturation in the blood of the subject, based on respective amplitudes of the signals $SM_R$, $SM_{IR}$, according to a predetermined expression pre-stored in the ROM 31. The blood oxygen saturation determining method is disclosed in U.S. Pat. No. 5,131,391.

Figure 2:
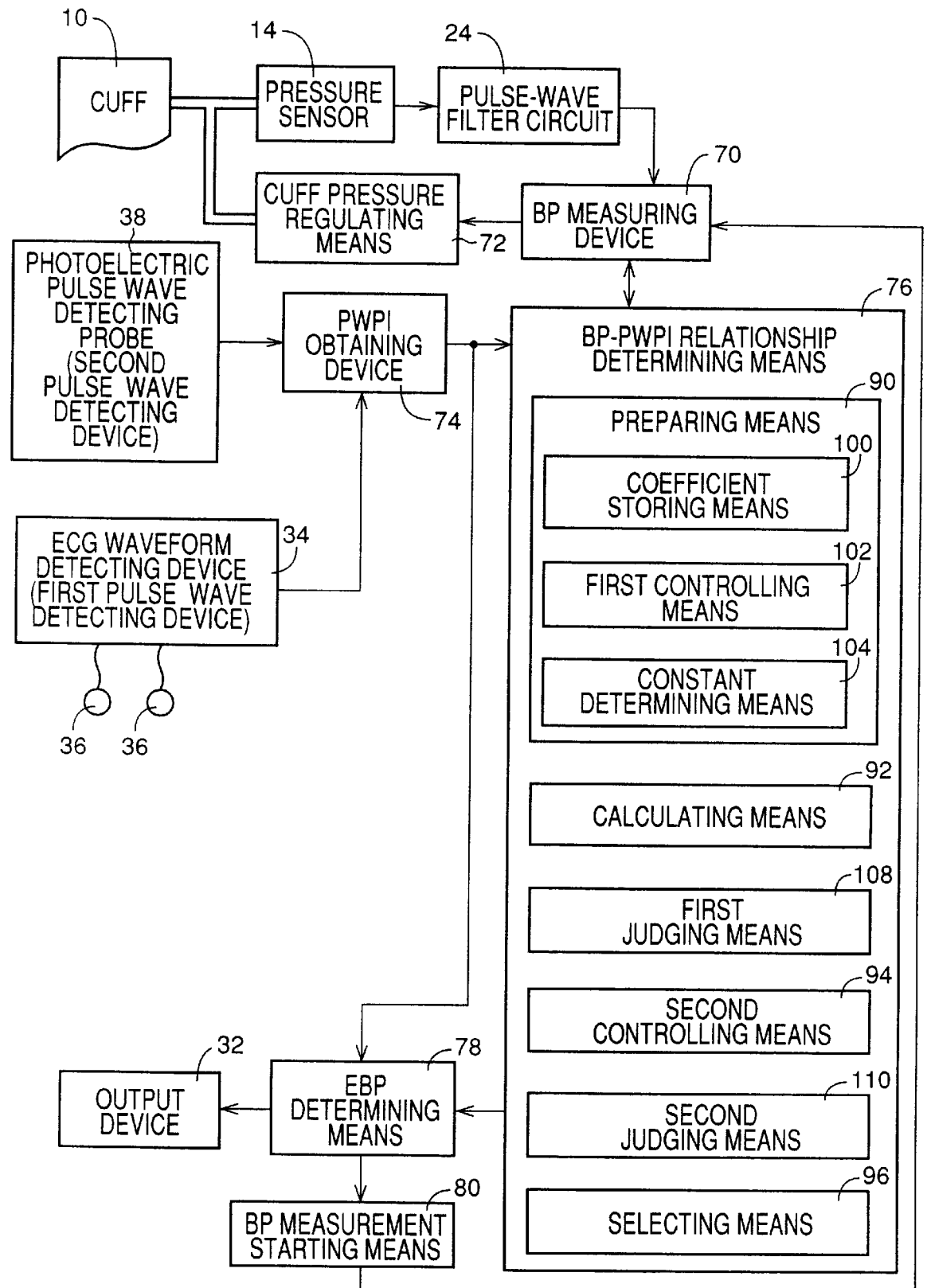
FIG. 2 is a block diagram for illustrating essential functions of an electronic control device 28 of the apparatus of FIG. 1.

FIG. 2 illustrates essential functions of the electronic control device 28 of the present BP monitor apparatus 8. In the figure, a blood pressure (BP) measuring device 70 measures a systolic, a mean and a diastolic blood pressure value $BP_{SYS}$, $BP_{MEAN}$, $BP_{DIA}$, of the subject, according to a well-known oscillometric method, based on variation of respective magnitudes of pulses of the pulse wave represented by the pulse-wave signal $SM_1$ obtained while the cuff pressure which is quickly increased, by a cuff pressure regulating means 72, to a target value $P_{CM}$ (e.g., 180 mmHg), is slowly decreased at the rate of about 3 mmHg/sec.

Figure 3:
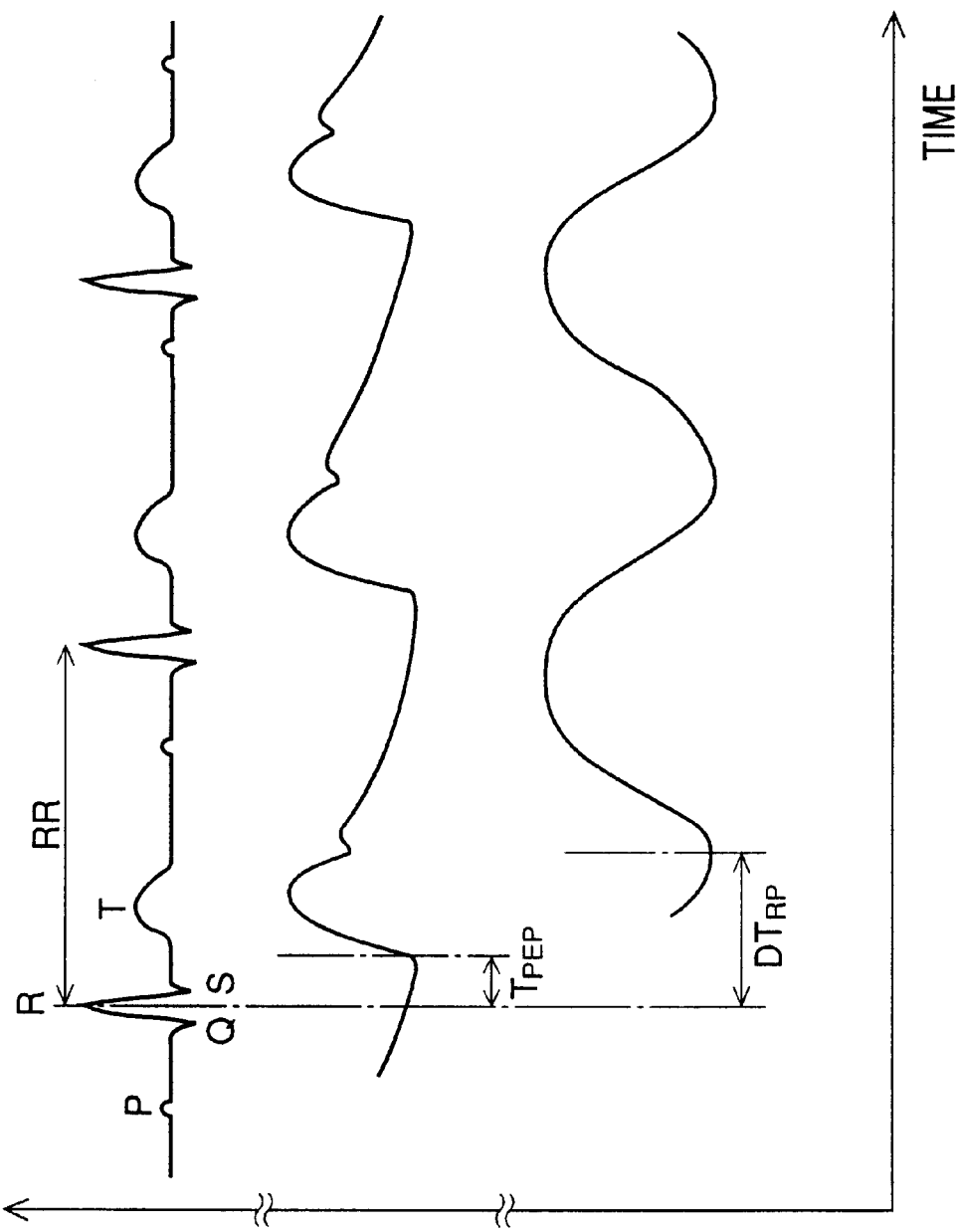
FIG. 3 is a view to show a time difference $DT_{RP}$ obtained by the operation of the electronic control device 28.

A pulse-wave propagation information (PWPI) obtaining device 74 includes a time-difference calculating means for calculating, as a pulse-wave propagation time $DT_{RP}$, a time difference between a predetermined point (e.g., R-wave) of the ECG waveform of each of periodic pulses successively detected by the ECG waveform detecting device 34 and a predetermined point (e.g., rising point or minimum point) of the waveform of a corresponding one of periodic pulses of the photoelectric pulse wave detected by the probe 38, as shown in FIG. 3. The PWPI obtaining device 74 further calculates a pulse-wave propagation velocity $V_M$ (m/sec) of the pulse wave propagated through the artery of the patient, based on the calculated pulse-wave propagation time $DT_{RP}$, according to the following expression (1) pre-stored in the ROM 31:

$$V_M = L/(DT_{RP} - T_{PEP}) \quad (1)$$

where L (m) is a length of the artery as measured from the left ventricle to the position at which the probe 38 is set, via the aorta; and $T_{PEP}$ (sec) is a pre-ejection period between the R-wave of the ECG waveform of each pulse and the minimum point of the waveform of a corresponding pulse of the aortic pulse wave. The values L and $T_{PEP}$ are constants, respectively, and are experimentally obtained in advance.

A blood pressure-pulse wave propagation information (BP-PWPI) relationship determining means 76 determines, in advance, two coefficients α, β in the following expressions (2) and (3), based on the systolic blood pressure value $BP_{SYS}$ measured by the BP measuring device 70 and either one of the pulse-wave propagation time $DT_{RP}$ and the pulse-wave propagation velocity $V_M$ (e.g., either one of respective average values of the pulse-wave propagation time values $DT_{RP}$ and the pulse-wave propagation velocity values $V_M$ obtained during each blood pressure measurement). The expressions (2) and (3) respectively show a relationship between systolic blood pressure $BP_{SYS}$ and pulse-wave propagation time $DT_{RP}$, and a relationship between systolic blood pressure $BP_{SYS}$ and pulse-wave propagation velocity $V_M$. In place of the relationship between systolic blood pressure $BP_{SYS}$ and either one of the pulse-wave propagation time $DT_{RP}$ and the pulse-wave velocity $V_M$, a relationship between a mean or a diastolic blood pressure measured by the BP measuring device 70 and either one of the pulse-wave propagation time $DT_{RP}$ and the pulse-wave velocity $V_M$ may be employed. In short, the blood pressure-pulse wave propagation information relationship may be determined depending upon which one of the systolic, mean and diastolic blood pressure value is selected as a monitor (estimated) blood pressure value EBP.

$$EBP = \alpha(DT_{RP}) + \beta \quad (2)$$

where α is a negative constant and β is a positive constant.

$$EBP = \alpha(V_M) + \beta \quad (3)$$

where α is a positive constant and β is a positive constant.

An estimated blood pressure (EBP) determining means 78 successively determines the estimated blood pressure value EBP of the subject, based on either one of the actual pulse-wave propagation time $DT_{RP}$ and pulse-wave propagation velocity $V_M$ successively obtained by the PWPI obtaining device 74, according to the blood pressure-pulse wave propagation information relationship (represented by the expression (2) or (3)). The electronic control device 28 controls a output device 32 to concurrently output the thus determined estimated blood pressure values EBP in a trend graph along a predetermined axis representative of time.

A blood pressure (BP) measurement starting means 80 starts a blood-pressure measurement of the BP measuring device 70, when a change of the estimated blood pressure value EBP exceeds a third reference value (a first and a second reference value will be described later). In short, the BP measurement starting means 80 may functions as an estimated-blood-pressure-abnormality judging means for judging that an estimated blood pressure value EBP determined by the EBP determining means 78 is abnormal when the estimated blood pressure value EBP is, by not less than a predetermined value or a predetermined ratio, greater or smaller than an actual blood pressure value measured at the prior blood pressure measurement using the cuff 10. For instance, when the estimated blood pressure value EBP is, by not less than a ratio of ±20%, greater or smaller than an actual blood pressure value measured at the prior blood pressure measurement, the BP measurement starting means 80 starts a blood pressure measurement of the BP measuring device 70.

The BP-PWPI relationship determining means 76 includes a preparing means 90, a calculating means 92, a second controlling means 94 (a first controlling means 102 will be described later) and a selecting means 96, so as to minimize the number of blood pressure measurements each using the cuff and determine a blood pressure-pulse wave propagation information relationship with high accuracy.

Figure 4:
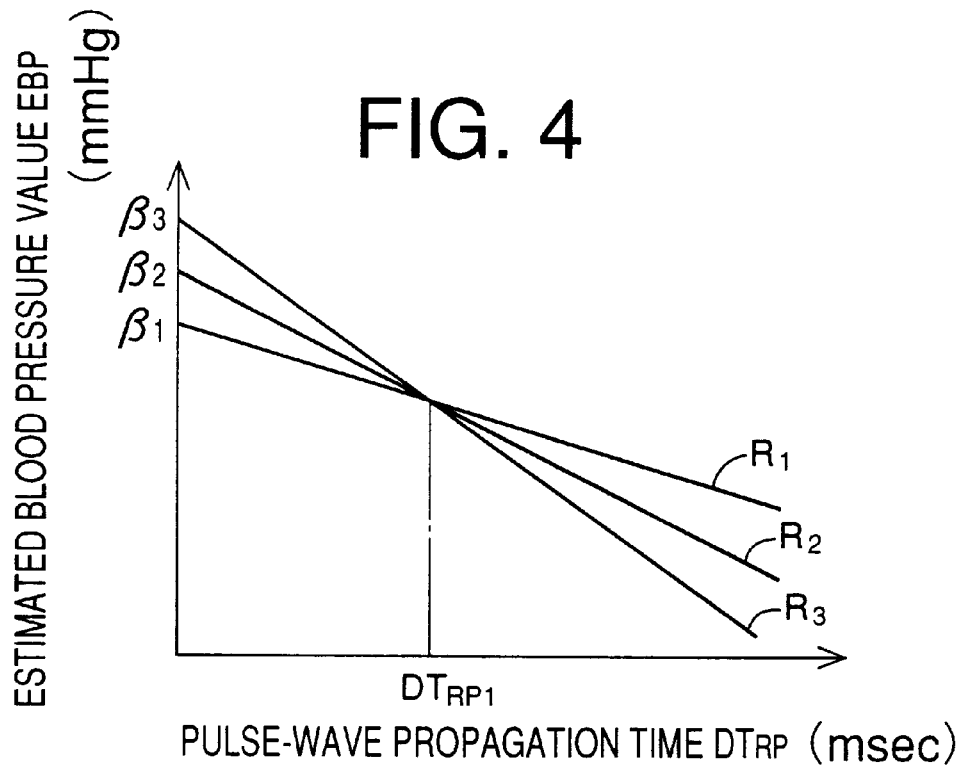
FIG. 4 is a view for explaining a plurality of candidates $R_1$, $R_2$, $R_3$ for a relationship between blood pressure and pulse-wave propagation information prepared in the apparatus of FIG. 1.
Figure 5:
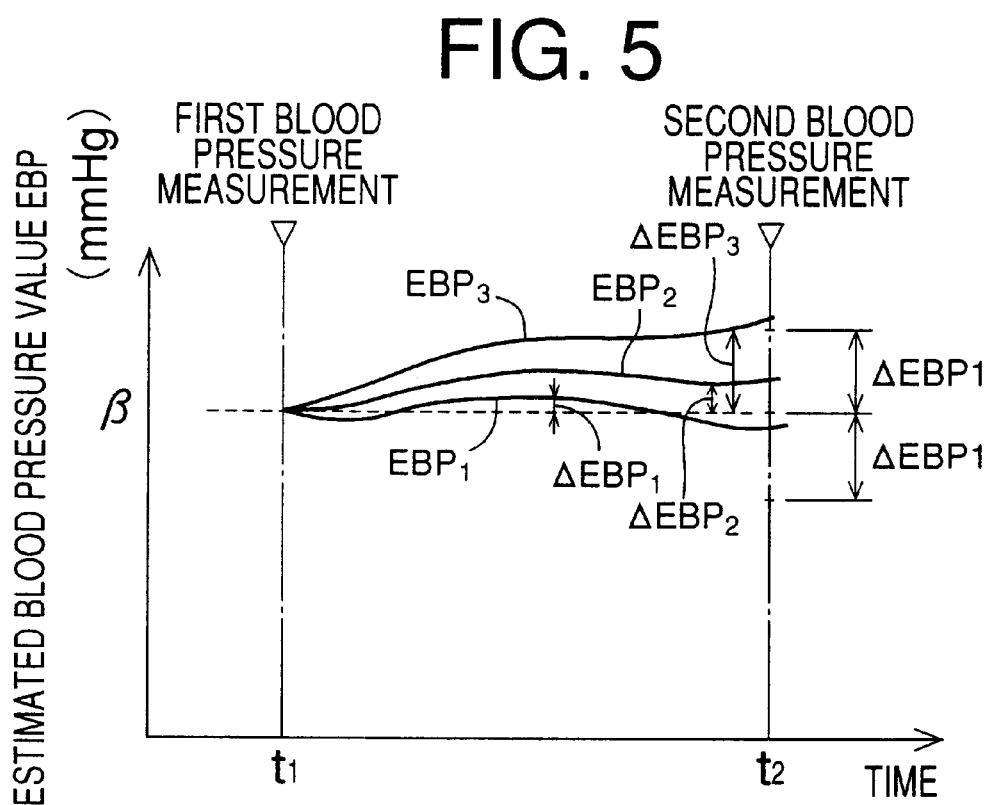
FIG. 5 is a view to show respective trend graphs of estimated blood pressure values $EBP_1$, $EBP_2$, $EBP_3$ which are successively calculated, based on each of successive actual pulse-wave propagation times $DT_{RP}$, according to the plurality of candidates $R_1$, $R_2$, $R_3$, respectively.
Figure 6:
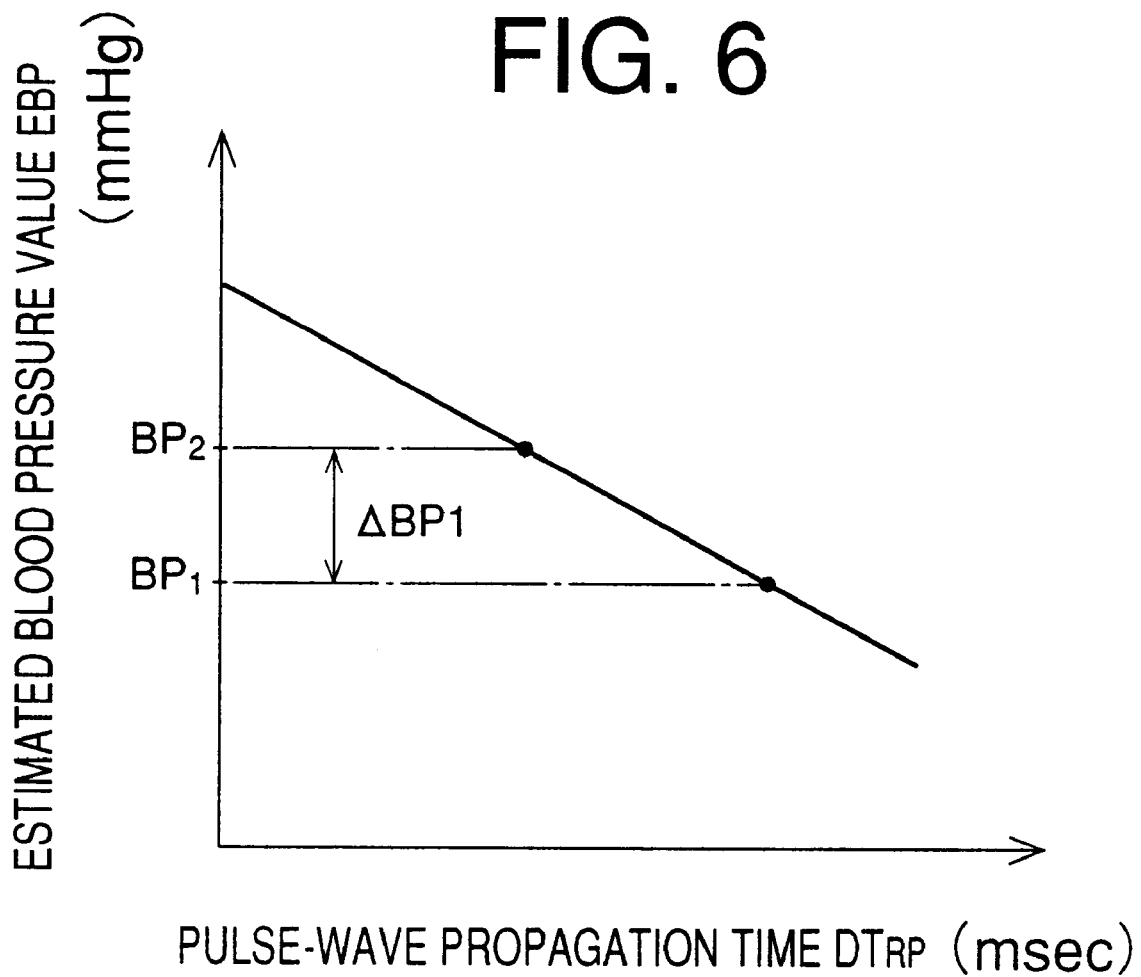
FIG. 6 is a view to show a relationship between blood pressure and pulse-wave propagation information which is selected from the plurality of candidates $R_1$, $R_2$, $R_3$ in the apparatus of FIG. 1.

The preparing means 90 prepares a plurality of candidates $R_m$ (m=1~i; i is natural number) for the relationship between blood pressure and pulse-wave propagation information used by the EBP determining means 78, as shown in FIG. 4. The calculating means 92 successively calculates a plurality of estimated blood pressure values $EBP_m$ (m=1~i), based on each of successive sets of actual pulse-wave propagation information (DT or $V_M$) of the subject, according to the plurality of candidates prepared by the preparing means 90, respectively, and thereby providing a plurality of groups of successively calculated estimated blood pressure values $EBP_m$ which correspond to the plurality of candidates $R_m$, respectively. The second controlling means 94 controls the BP measuring device 70 to measure an actual blood pressure value of the subject, when at least one of absolute values of respective changes ΔEBP of the plurality of groups of estimated blood pressure values provided by the calculating means 92 exceeds a first reference value ΔEBP1, as shown in FIG. 5. The selecting means 96 selects, as the relationship between blood pressure and pulse-wave propagation information, one of the plurality of candidates $R_m$ which corresponds to one of the plurality of groups of estimated blood pressure values $EBP_m$ which includes the estimated blood pressure value that is the most approximate to the actual blood pressure value measured by the BP measuring device 70 under control of the second controlling means 94, as shown in FIG. 6.

Each of the plurality of candidates $R_m$ comprises the following expression: $EBP = \alpha(PWPI) + \beta$, where EBP is blood pressure, PWPI is pulse-wave propagation information, α is a coefficient and β is a constant. The preparing means 90 includes a coefficient storing means 100, a first controlling means 102 and a constant determining means 104. The coefficient storing means 100 stores a plurality of coefficients $\alpha_m$ (m=1~i) predetermined for the plurality of candidates $R_m$ with a certain degree of accuracy, respectively. The first controlling means 102 controls the BP measuring device 70 to measure a first actual blood pressure value $BP_1$ of the subject. The constant determining means 104 determines a plurality of constants $\beta_m$ (m=1~i) for the plurality of candidates $R_m$, respectively, by substituting the plurality of predetermined coefficients for the respective coefficients of the plurality of candidates $R_m$ and substituting the blood pressure value measured at the prior blood pressure measurement using the cuff (e.g., first blood pressure value) and a set of actual pulse-wave propagation information for the blood pressure and the pulse-wave propagation information of each of the candidates $R_m$, as shown in FIG. 4.

$$EBP_1 = \alpha_1 DT_{RP} + \beta_1 \ldots (R_1)$$

$$EBP_2 = \alpha_2 DT_{RP} + \alpha_2 \ldots (R_2)$$

$$EBP_3 = \alpha_3 DT_{RP} + \beta_3 \ldots (R_3) \quad (4)$$

The above described expressions (4) and FIG. 4 show three relationships $R_m$ (i=3) between blood pressure and pulse-wave propagation information $DT_{RP}$, for example.

To efficiently carry out a blood pressure measurement using the cuff 10 for determining the relationship between blood pressure and pulse-wave propagation information after detection of a sufficiently large blood pressure change of the subject, a first judging means 108 judges whether at least one of absolute values of the respective changes $\Delta EBP_m$ of the plurality of groups of estimated blood pressure values $EBP_m$ from the blood pressure value measured at the prior blood pressure measurement using the cuff (e.g., first actual blood pressure value) exceeds the first reference value $\Delta EBP1$. The second controlling means 94 controls the BP measuring device 70 to measure a second actual blood pressure value $BP_2$ of the subject, when the first judging means makes a positive judgment. The first reference value $\Delta EBP1$ is a criterion for finding a sufficiently large blood pressure change of the subject. The first reference value $\Delta EBP1$ may be a value such as 20% of the blood pressure value measured at the prior blood pressure measurement using the cuff (e.g., first actual blood pressure value).

To maximize the accuracy of the relationship between blood pressure and pulse-wave propagation information, it is desirable that an absolute value of a change of the second actual blood pressure value $BP_2$ from the blood pressure value measured at the prior blood pressure measurement using the cuff (e.g., first actual blood pressure value $BP_1$) be sufficiently large. Therefore, a second judging means 110 judges whether the absolute value of the change $\Delta BP$ of the second actual blood pressure value $BP_2$ is greater than a second reference value $\Delta BP1$.

When the second judging means 110 judges whether the absolute value of the change $\Delta BP$ of the second actual blood pressure value $BP_2$ is not greater than the second reference value $\Delta BP1$, i.e., makes a negative judgment, the constant determining means 104 determines a plurality of constants $\beta_m$ for the plurality of candidates $R_m$, respectively, based on the second blood pressure value, the calculating means 92 successively calculates a plurality of estimated blood pressure values $EBP_m$, based on each of successive sets of actual pulse-wave propagation information of the subject, according to the plurality of candidates $R_m$, respectively, and thereby providing a plurality of groups of successively calculated estimated blood pressure values $EBP_m$ which correspond to the plurality of candidates $R_m$, respectively, the first judging means 108 judges whether at least one of absolute values of the respective changes $\Delta EBP$ of the plurality of groups of estimated blood pressure values from the second actual blood pressure value $BP_2$ exceeds a first reference value $\Delta EBP1$, and the second controlling means 94 controls the BP measuring device to measure a third actual blood pressure value of the subject.

Meanwhile, when the second judging means 110 makes a positive judgment, the selecting means 96 selects, as the relationship between blood pressure and pulse-wave propagation information, one of the plurality of candidates $R_m$ which corresponds to one of the plurality of groups of estimated blood pressure values $EBP_m$ which includes the estimated blood pressure value that is the most approximate to the second actual blood pressure value $BP_2$ measured by the BP measuring device 70 under control of the second controlling means 94, as shown in FIG. 6.

Next, there will be described the operation of the electronic control device 28 of the BP monitor apparatus 8 by reference to the flow charts of FIGS. 7 and 8.

Figure 7:
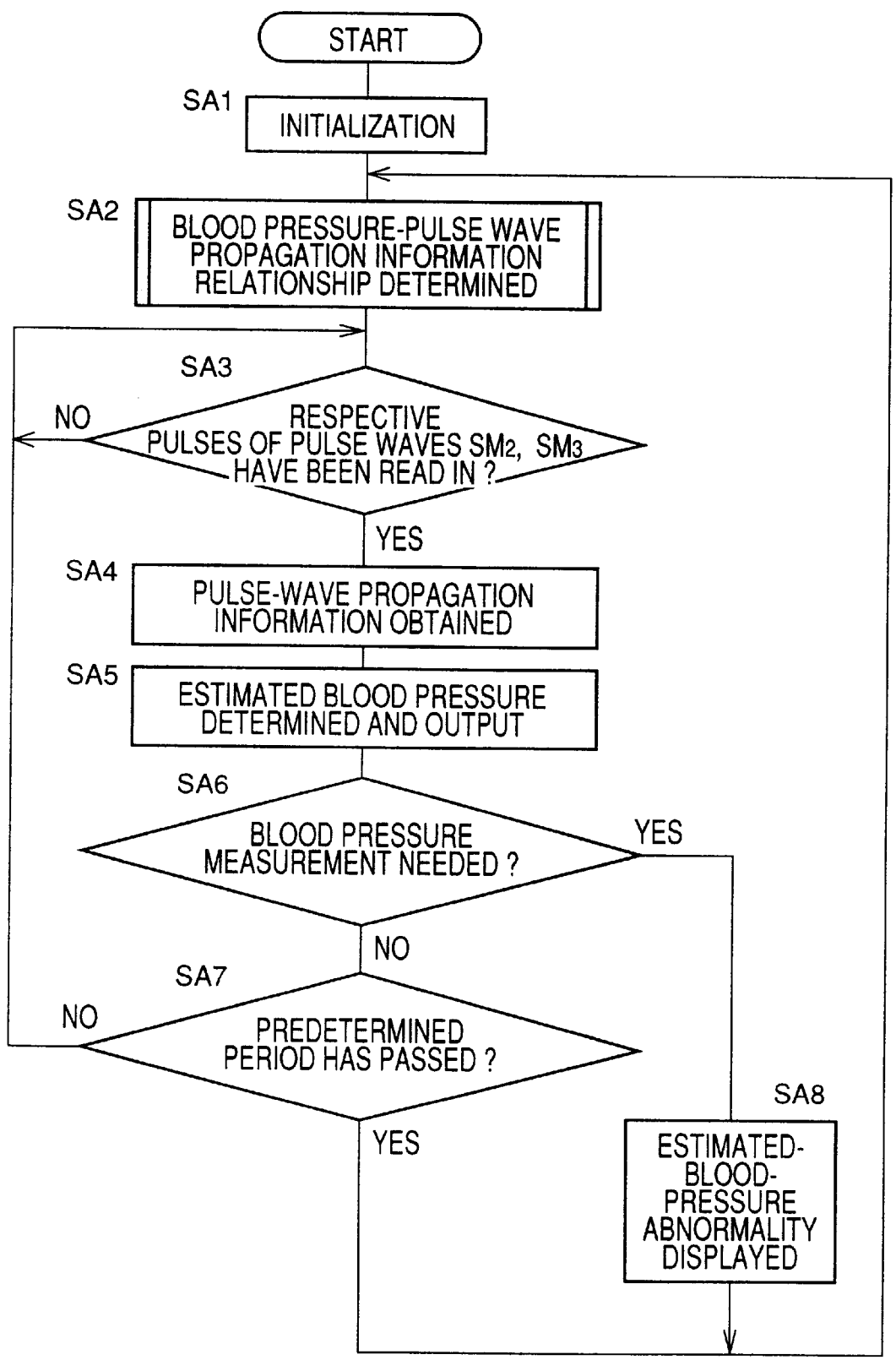
FIG. 7 is a flow chart representing a control program, i.e., a blood pressure monitor routine, according to which the apparatus of FIG. 1 is operated.

The control of the CPU 29 begins with Step SA1 of the flow chart of FIG. 7, where flags, counters and registers (which are not shown) are reset. The control of the CPU 29 goes to Step SA2 corresponding to the selecting means 96. At Step SA2, the CPU 29 carries out a blood pressure-pulse wave propagation information (BP-PWPI) relationship determining routine shown in FIG. 8 so as to select, from a plurality of candidates, a relationship between blood pressure-pulse wave propagation information.

Figure 8:
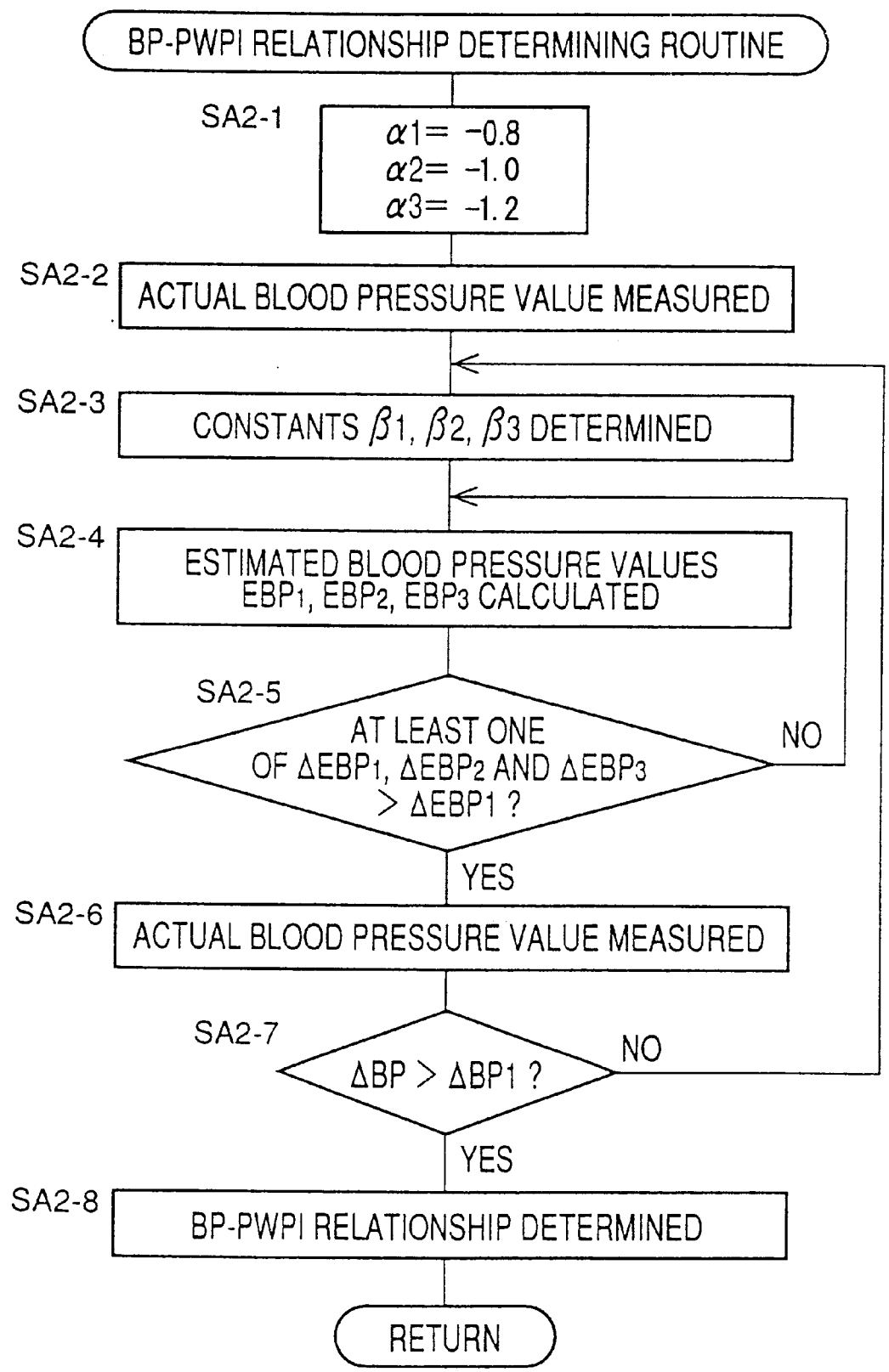
FIG. 8 is a flow chart representing a blood pressure-pulse wave propagation information relationship determining routine carried out at Step SA2 of FIG. 7.

At Step SA2-1 of FIG. 8, the CPU 29 retrieves, from the RAM 33, a plurality of predetermined coefficients $\alpha_m$, and first and second reference values $\Delta EBP1$, $\Delta BP1$, which have been input and pre-stored in the RAM 33. There will be described below the case of i=3 where values $\alpha_1$, $\alpha_2$, $\alpha_3$ are obtained as the plurality of coefficients $\alpha_m$. For example, the values all $\alpha_1$, $\alpha_2$, $\alpha_3$ may be −0.8, −1.0 and −1.2, respectively.

Step SA2-1 is followed by Step SA2-2 to control the BP measuring device 70 to measure a first actual blood pressure value $BP_1$. Step SA2-2 corresponds to the first controlling means 102. The blood pressure measurement using the cuff 10 is carried out as described below. The CPU 29 calculates, as a pulse-wave propagation time $DT_{RP}$, a time difference between an R-wave of the ECG waveform of a pulse and a rising point of the waveform of a corresponding pulse of the photoelectric pulse wave, and then calculate a pulse-wave propagation velocity $V_M$ (m/sec) based on the calculated pulse-wave propagation time $DT_{RP}$ according to the expression (1) before the increasing of the cuff pressure. Then the CPU 29 starts to quickly increase the cuff pressure for a blood pressure measurement, by switching the selector valve 16 to the inflation position and operating the air pump 18, and when it is judged that the cuff pressure $P_C$ is equal to or greater than a predetermined target value $P_{CM}$ (e.g., 180 mmHg), the CPU 29 carries out a blood pressure measuring algorithm. More specifically, the air pump 18 is stopped and the selector value 16 is switched to the slow-deflation position where the selector valve 16 permits the pressurized air to be slowly discharged from the cuff 10. A systolic blood pressure value $BP_{SYS}$, a mean blood pressure value $BP_{MEAN}$ and a diastolic blood pressure value $BP_{DIA}$ are determined, according to a well known oscillometric type blood pressure determining algorithm, based on the variation of respective amplitudes of pulses of the pulse wave represented by the pulse wave signal $SM_1$ obtained while the cuff pressure is slowly decreased at a predetermined rate of about 3 mmHg/sec. The thus measured blood pressure values are output on the output device 32, and the selector valve 16 is switched to the quick-deflation position where the selector valve 16 permits the pressurized air to be quickly discharged from the cuff 10.

Step SA2-2 is followed by Step SA2-3 to determine a plurality of constants $\beta_1$, $\beta_2$, $\beta_3$ for three candidates $R_1$, $R_2$, $R_3$, respectively, by substituting the three predetermined coefficients $\alpha_1$, $\alpha_2$, $\alpha_3$ for the respective coefficients of the three candidates $R_1$, $R_2$, $R_3$ and substituting the first actual blood pressure value $BP_1$ and the actual pulse-wave propagation information time $DT_{RP}$ obtained in the blood pressure measurement at Step SA2-2 (at time point $t_1$ of FIG. 5) for the blood pressure and the pulse-wave propagation information of each of the three candidates. Step SA2-3 corresponds to the constant determining means 104.

Step SA2-3 is followed by Step SA2-4 to successively calculate three estimated blood pressure values $EBP_1$, $EBP_2$, $EBP_3$, based on each of successive pulse waves, i.e., each of successive actual pulse-wave propagation times $DT_{RP}$ calculated in synchronism with detection of each of the successive pulse waves, according to the three candidates $R_1$, $R_2$, $R_3$ shown in FIG. 4, respectively, and thereby providing three groups of successively calculated estimated blood pressure values which correspond to the three candidates, respectively. Step SA2-4 corresponds to the calculating means 92. FIG. 5 is a view to show respective trend graphs of the three groups of estimated blood pressure values $EBP_1$, $EBP_2$, $EBP_3$ which are successively calculated based on the successive pulse waves.

Step SA2-4 is followed by Step SA2-5 to judge whether or not at least one of absolute values of the respective changes $\Delta EBP_1$, $\Delta EBP_2$, $\Delta EBP_3$ of the three groups of estimated blood pressure values $EBP_1$, $EBP_2$, $EBP_3$ from the first actual blood pressure value $BP_1$ measured at Step SA2-2 exceeds a first reference value $\Delta EBP1$ such as 20% of the first actual blood pressure value $BP_1$. Step SA2-5 corresponds to the first judging means 108. If a negative judgment is made at Step SA2-5, the control of the CPU 29 goes back to Step SA2-4. If a positive judgment is made at Step SA2-5, the control of the CPU 29 goes to Step SA2-6 to control the BP measuring device 70 to measure a second actual blood pressure value $BP_2$ of the subject, in the same manner as carried out at Step SA2-2. Time point $t_2$ in FIG. 5 indicates a time when the second actual blood pressure value $BP_2$ is measured by the BP measuring device 70. Step SA2-6 corresponds to the second controlling means 94.

Step SA2-6 is followed by Step SA2-7 to judge whether or not an absolute value of a change $\Delta BP$ of the second actual blood pressure value $BP_2$ from the first actual blood pressure value $BP_1$ is greater than a second reference value $\Delta BP1$ such as 20 mmHg which is greater than a blood-pressure change generated in synchronism with a respiration of the subject. Step SA2-7 corresponds to the second judging means 110. If a negative judgment is made at Step SA2-7, i.e., a difference between the first and second go blood pressure values $BP_1$, $BP_2$ is not so large, the control of the CPU 29 goes back to Step SA2-3. If a positive judgment is made at Step SA2-7, the control of the CPU 29 goes to Step SA2-8 corresponding to the selecting means 96. At Step SA2-8, the CPU 29 selects, as the relationship between blood pressure and pulse-wave propagation information, one of the three candidates which corresponds to one of the three groups of estimated blood pressure values which includes the estimated blood pressure value that is the most approximate to the second actual blood pressure value $BP_2$ measured at Step SA2-6.

When the relationship between blood pressure and pulse-wave propagation information is determined in the above described BP-PWPI relationship determining routine, the control of the CPU 29 goes to Step SA3 of FIG. 7. At Step SA3, the CPU 29 judge whether or not the R-wave of the ECG waveform of a pulse and the waveform of a corresponding pulse of the photoelectric pulse wave have been read in. If a negative judgment is made at Step SA3, the control of the CPU 29 waits until a positive judgment is made at Step SA3. If a positive judgment is made at Step SA3, the control of the CPU 29 goes to Step SA4 corresponding to the PWPI obtaining device 74. At Step SA4, the CPU 29 calculates a pulse-wave propagation time $DT_{RP}$ and a pulse-wave propagation velocity $V_M$ based on the R-wave of the ECG waveform and the waveform of the photoelectric pulse wave read in at Step SA3, in the same manner as carried out at Step SA2.

Step SA4 is followed by Step SA5 corresponding to the EBP determining means 78. At Step SA5, the CPU 29 determines an estimated blood pressure value EBP (a systolic, a mean or a diastolic blood pressure value), based on the pulse-wave propagation time $DT_{RP}$ calculated at Step SA4, according to the blood pressure-pulse wave propagation information relationship determined at Step SA2. Further, the CPU 29 outputs, on the output device 32, a trend graph of the estimated blood pressure values EBP determined for respective pulses of the ECG waveform and the photoelectric pulse wave.

Step SA5 is followed by Step SA6 corresponding to the BP measurement starting means 80. At Step SA6, the CPU 29 starts a blood pressure measurement of the BP measuring device 70, when the estimated blood pressure value EBP is, by not less than a ratio of from 20% to 25%, greater or smaller than the actual blood pressure value measured at the prior blood pressure measurement using the cuff. If a negative judgment is made at Step SA6, the control of the CPU 29 goes to Step SA7. At Step SA7, the CPU 29 judges whether or not a predetermined period (e.g., 15 to 20 minutes), that is, a calibration period, has passed after the prior blood pressure measurement. If a negative judgment is made at Step SA7, the control of the CPU goes back to Step SA3 and the following steps so as to carry out the blood pressure monitor routine, that is, determine an estimated blood pressure value EBP for each pulse, and timewise output, on the output device 32, the trend graph of the determined estimated blood pressure values EBP.

On the other hand, if a positive judgment is made at Step SA6, the control of the CPU 29 goes to Step SA8. At Step SA8, the CPU 29 outputs an estimated-blood-pressure abnormality on the output device 32. Then, the control of the CPU 29 goes back to Step SA2 to start a blood pressure measurement using the cuff 10 and determine a new relationship between blood pressure and pulse-wave propagation information.

In the above described embodiment, the calculating means 92 (Step SA2-4) successively calculates a plurality of estimated blood pressure values $EBP_1$, $EBP_2$, $EBP_3$, based on each pulse-wave propagation time $DT_{RP}$, according to the plurality of candidates $R_1$, $R_2$, $R_3$ prepared by the preparing means 90 (Steps SA2-1 to SA2-3), respectively, and thereby providing a plurality of groups of successively calculated estimated blood pressure values which correspond to the plurality of candidates, respectively. The second controlling means 94 (Step SA2-6) controls the BP measuring device 70 to measure a second actual blood pressure value of the subject, when at least one of absolute values of respective changes $\Delta EBP_1$, $\Delta EBP_2$, $\Delta EBP_3$ of the plurality of groups of estimated blood pressure values $EBP_1$, $EBP_2$, $EBP_3$ provided by the calculating means 92 exceeds the first reference value $\Delta EBP1$. The selecting means 96 (Step SA2-8) selects, as the relationship between blood pressure and pulse-wave propagation information, one of the plurality of candidates which corresponds to one of the plurality of groups of estimated blood pressure values $EBP_1$, $EBP_2$, $EBP_3$ which includes the estimated blood pressure value that is the most approximate to the second actual blood pressure value measured by the BP measuring device 70 under control of the second controlling means 94. Thus, in the BP monitor apparatus 8, a blood pressure measurement using the cuff is carried out in response to a sufficiently large change of a blood pressure of the subject, and accordingly it is possible to minimize the number of blood pressure measurements and determine the relationship between blood pressure and pulse-wave propagation information with high accuracy.

In the above described embodiment, the preparing means 90 includes the coefficient storing means 100 (Step SA2-1), the first controlling means 102 (Step SA2-2) and the constant determining means 104 (Step SA2-3). The coefficient storing means 100 stores a plurality of predetermined coefficients for the plurality of candidates, respectively. The first controlling means 102 controls the BP measuring device 70 to measure a first actual blood pressure value of the subject. The constant determining means 104 determines a plurality of constants $\beta_1$, $\beta_2$, $\ominus_3$ for the plurality of candidates $R_1$, $R_2$, $R_3$, respectively, by substituting the plurality of predetermined coefficients $\alpha_1$, $\alpha_2$, $\alpha_3$ for the respective coefficients of the plurality of candidates and substituting the blood pressure value measured at the prior blood pressure measurement and the actual pulse-wave propagation time $DT_{RP}$ for the blood pressure and pulse-wave propagation information of each of the candidates. Thus, the BP monitor apparatus 8 can prepare the plurality of candidates with a certain degree of accuracy, for the relationship between blood pressure and pulse-wave propagation information.

In the above described embodiment, the control device 28 functions as the first judging means 108 (Step SA2-5) and the second controlling means 94. The first judging means 108 judges whether or not at least one of absolute values of the respective changes $\Delta EBP_1$, $\Delta EBP_2$, $\Delta EBP_3$ of the plurality of groups of estimated blood pressure values $EBP_1$, $EBP_2$, $EBP_3$ from the actual blood pressure value measured at the prior blood pressure measurement exceeds the first reference value $\Delta EBP1$. The second controlling means 94 controls the BP measuring device 70 to measure a second actual blood pressure value of the subject, when the first judging means makes a positive judgment. Thus, the BP monitor apparatus 8 can carry out a blood pressure measurement using the cuff for determining the relationship between blood pressure and pulse-wave propagation information, after detection of the sufficiently large blood pressure change of the subject.

In the above described embodiment, the selecting means 96 includes the second judging means 110 (Step SA2-7) which judges whether or not an absolute value of a change $\Delta BP$ of the current actual blood pressure value from the actual blood pressure value measured at the prior blood pressure measurement is greater than the second reference value $\Delta BP1$. When the second judging means 110 makes a negative judgment, the constant determining means 104 determines a plurality of constants $\beta_m$ for the plurality of candidates $R_m$, respectively, based on the current blood pressure value, the calculating means 92 successively calculates a plurality of estimated blood pressure values $EBP_m$, based on each set of actual pulse-wave propagation information $(DT_{RP1})$, according to the plurality of candidates $R_m$, respectively, and thereby providing a plurality of groups of successively calculated estimated blood pressure values which correspond to the plurality of candidates, respectively, the first judging means 108 judges whether at least one of the absolute values of the respective changes $\Delta EBP_m$ of the plurality of groups of estimated blood pressure values from the above-indicated current actual blood pressure value exceeds the first reference value $\Delta EBP1$, and the second controlling means controls the BP measuring device 70 to measure a new actual blood pressure value of the subject. When the second judging means 110 makes a positive judgment, the selecting means 96 selects, as the relationship between blood pressure and pulse-wave propagation information, one of the plurality of candidates $R_m$ which corresponds to one of the plurality of groups of estimated blood pressure values which includes the estimated blood pressure value that is the most approximate to the above-indicated current actual blood pressure value $BP_2$ measured by the BP measuring device 70 under control of the second controlling means 94. Thus, in the BP monitor apparatus 8, when the absolute value of the change of the current actual blood pressure value from the prior actual blood pressure value is greater than the second reference value $\Delta BP1$, an operation of the selecting means 94 is carried out. Thus, the accuracy of the relationship between blood pressure and pulse-wave propagation information is raised.

While the present invention has been described in its preferred embodiments by reference to the drawings, it is to be understood that the invention may otherwise be embodied.

While in the illustrated embodiment of FIGS. 7 and 8 the relationship between blood pressure and pulse-wave propagation time $DT_{RP}$ is employed, a relationship between blood pressure and pulse-wave propagation velocity $V_M$ may be employed. In the latter case, the straight lines shown in FIGS. 4 and 6 is are replaced by straight lines whose slopes are positive.

While in the illustrated embodiment the liner expression is employed as the relationship between blood pressure and pulse-wave propagation information, a quadratic or higher polynomial expression may be employed.

While in the illustrated embodiment the BP measuring device 70 employs the so-called oscillometric method, it is possible to employ a so-called Korotokoff-sound method which determines, as a systolic and a diastolic blood pressure value, respective cuff pressures at the time of occurrence and disappearance of Korotokoff-sounds.

While in the illustrated embodiment the photoelectric pulse wave detecting probe 38 is used as the peripheral pulse wave detecting device, an impedance sensor being set on a finger of a living subject for detecting the change of impedance of the subject, a pressure pulse wave measuring device being adapted to be pressed on a radial artery of a subject for measuring a pressure in the radial artery of the subject, or the like may be used. In short, any pulse wave representative of circulation dynamics of a peripheral body portion of a subject may be detected and utilized.

While in the illustrated embodiment the pulse-wave propagation time $DT_{RP}$ or the pulse-wave propagation velocity $V_M$ is calculated, based on the time difference between the predetermined point of the ECG waveform detected by the ECG waveform detecting device 34 and the predetermined point of the waveform of the photoelectric pulse wave detected by the photoelectric pulse wave probe 38, the pulse-wave propagation time $DT_{RP}$ or the pulse-wave propagation velocity $V_M$ may be calculated using a first pulse wave detecting device being set on a carotid artery or a brachial artery of the subject and a second pulse wave detecting device being set on a wrist or a finger of the subject, in place of the ECG waveform detecting device 34 and the photoelectric pulse wave probe 38.

While in the illustrated embodiment the photoelectric pulse wave detecting probe 38 is used as the second pulse wave detecting device, it is possible to employ a cuff pulse wave sensor which detects a cuff pulse wave from the cuff 10 being held at a predetermined cuff pressure, a pressure pulse-wave sensor which is adapted to be pressed on a radial artery of a subject and detects a pressure pulse wave from the artery, an impedance pulse-wave sensor which detects, through electrodes, an impedance pulse wave from an arm or an end portion of a finger of a subject, a light-transmission type photoelectric pulse wave sensor which is adapted to be set on a finger of a subject and detects a photoelectric pulse wave from the finger, or the like.

In the illustrated embodiment, the pulse-wave propagation velocity $V_M$ is calculated based on the time difference between the R-wave of the ECG waveform and the rising point of the waveform of the photoelectric pulse wave. However, the pulse-wave propagation velocity $V_M$ may be calculated-based on a time difference between a Q-wave of the ECG waveform of each pulse and the rising point of the waveform of a corresponding pulse of the photoelectric pulse wave.

In the illustrated embodiment, an estimated blood pressure EBP is determined based on the R-wave of the ECG waveform of each pulse or the waveform of each pulse of the photoelectric pulse wave. However, an estimated blood pressure EBP may be determined based on every second pulse, or so on, of the ECG waveform or the photoelectric pulse wave.

It is to be understood that the present invention may be embodied with other changes and modifications that may occur to those skilled in the art without departing from the scope of the invention.

What is claimed is:

1. A blood pressure monitor apparatus comprising:

a blood pressure measuring device which includes a cuff and measures an actual blood pressure value of a living subject by changing a pressing pressure of the cuff applied to a body portion of the subject;

estimated blood pressure determining means for successively determining an estimated blood pressure value of the subject, based on each of successive sets of actual pulse-wave propagation information of the subject, according to a relationship between blood pressure and pulse-wave propagation information;

preparing means for preparing a plurality of candidates for said relationship between blood pressure and pulse-wave propagation information;

calculating means for successively calculating a plurality of estimated blood pressure values, based on each of successive sets of actual pulse-wave propagation information of the subject, according to said plurality of candidates prepared by said preparing means, respectively, and thereby providing a plurality of groups of successively calculated estimated blood pressure values which correspond to said plurality of candidates, respectively;

starting means for controlling said blood pressure measuring device to measure an actual blood pressure value of the subject, when at least one of respective changes of said plurality of groups of estimated blood pressure values provided by said calculating means exceeds a first reference value; and selecting means for selecting, as said relationship between blood pressure and pulse-wave propagation information, one of said plurality of candidates which corresponds to one of said plurality of groups of estimated blood pressure values which includes the estimated blood pressure value that is most approximate to said actual blood pressure value measured by said blood pressure measuring device under control of said starting means.

2. A blood pressure monitor apparatus according to claim 1, wherein each of said plurality of candidates comprises the following expression: $EBP=\alpha(PWPI)+\beta$, where EBP is blood pressure, PWPI is pulse-wave propagation information, $\alpha$ is a coefficient and $\beta$ is a constant.

3. A blood pressure monitor apparatus according to claim 2, wherein said preparing means comprises:

coefficient storing means for storing a plurality of predetermined coefficients for said plurality of candidates, respectively;

first controlling means for controlling said blood pressure measuring device to measure a first actual blood pressure value of the subject; and constant determining means for determining a plurality of constants for said plurality of candidates, respectively, by substituting said plurality of predetermined coefficients for the respective coefficients of said plurality of candidates and substituting said first blood pressure value and a set of actual pulse-wave propagation information for the blood pressure and the pulse-wave propagation information of each of said candidates.

4. A blood pressure monitor apparatus according to claim 3, wherein said starting means comprises:

first judging means for judging whether at least one of said respective changes of said plurality of groups of estimated blood pressure values from said first actual blood pressure value exceeds said first reference value; and second controlling means for controlling said blood pressure measuring device to measure a second actual blood pressure value of the subject, when said first judging means makes a positive judgment.

5. A blood pressure monitor apparatus according to claim 4, wherein said selecting means comprises second judging means for judging whether a change of said second actual blood pressure value from said first actual blood pressure value is greater than a second reference value, wherein when said second judging means makes a negative judgment, said constant determining means determines a plurality of constants for said plurality of candidates, respectively, based on the second blood pressure value, said calculating means successively calculates a plurality of estimated blood pressure values, based on each of successive sets of actual pulse-wave propagation information of the subject, according to said plurality of candidates, respectively, and thereby providing a plurality of groups of successively calculated estimated blood pressure values which correspond to said plurality of candidates, respectively, said first judging means judges whether at least one of said respective changes of said plurality of groups of estimated blood pressure values from said second actual blood pressure value exceeds said first reference value, and said second controlling means controls said blood pressure measuring device to measure a third actual blood pressure value of the subject when said first judging means makes a positive judgment, and wherein when said second judging means makes a positive judgment, said selecting means selects, as said relationship between blood pressure and pulse-wave propagation information, said one of said plurality of candidates which corresponds to one of said plurality of groups of estimated blood pressure values which includes the estimated blood pressure value that is most approximate to said third actual blood pressure value measured by said blood pressure measuring device under control of said second controlling means.

6. A blood pressure monitor apparatus according to claim 1, further comprising an information obtaining device which obtains said each set of actual pulse-wave propagation information of the subject.

7. A blood pressure monitor apparatus according to claim 6, wherein said information obtaining device comprises:
   a first pulse wave detecting device which detects a first pulse wave from a first portion of the subject;
   a second pulse wave detecting device which detects a second pulse wave from a second portion of the subject; and
   time difference calculating means for calculating, as said each set of pulse-wave propagation information, a time difference between a periodic point of a waveform of each of heartbeat-synchronous pulses of the first pulse wave and a periodic point of a waveform of a corresponding one of heartbeat-synchronous pulses of the second pulse wave.

8. A blood pressure monitor apparatus according to claim 7, wherein said information obtaining device further comprises propagation velocity calculating means for calculating, as said each set of pulse-wave propagation information, a pulse-wave propagation velocity based on the time difference calculated by said time difference calculating means, according to a predetermined relationship between pulse-wave propagation velocity and time difference.

9. A blood pressure monitor apparatus according to claim 7, wherein said first pulse wave detecting device comprises an electrocardiographic waveform detecting device which includes a plurality of electrodes which are adapted to be set on predetermined locations of the first portion of the subject and which detects, as the first pulse wave, an electrocardiographic waveform from the subject through said electrodes.

10. A blood pressure monitor apparatus according to claim 9, wherein said second pulse wave detecting device comprises a volume pulse wave detecting device which detects a volume pulse wave from the second portion of the subject.

11. A blood pressure monitor apparatus according to claim 10, wherein said time difference calculating means comprises means for calculating, as said each set of pulse-wave propagation information, a time difference between an R point of each heartbeat-synchronous pulse of the electrocardiographic waveform and a lower-peak point of a corresponding heartbeat-synchronous pulse of the volume pulse wave.

12. A blood pressure monitor apparatus according to claim 1, wherein said starting means comprises:
   abnormality judging means for judging whether each of the estimated blood pressure values successively determined by the estimated blood pressure determining means is an abnormal value which does not fall within a reference range; and
   control means for controlling, when said abnormality judging means makes a positive judgment, said blood pressure measuring device to measure an actual blood pressure value of the subject.

13. A blood pressure monitor apparatus according to claim 12, further comprising an output device which outputs information indicating that said abnormality judging means makes the positive judgment.

14. A blood pressure monitor apparatus according to claim 12, wherein said preparing means comprises means for preparing a plurality of candidates based on the actual blood pressure value measured in response to the positive judgment of said abnormality judging means.

15. A blood pressure monitor apparatus according to claim 1, wherein said starting means comprises:
   time-duration judging means for judging whether a predetermined time duration has passed since a prior blood pressure measurement of said blood pressure measuring device; and
   control means for controlling, when said time-duration judging means makes a positive judgment, said blood pressure measuring device to measure an actual blood pressure value of the subject.

16. A blood pressure monitor apparatus according to claim 15, wherein said preparing means comprises means for preparing said plurality of candidates based on the actual blood pressure value measured in response to the positive judgment of said time-duration judging means.

17. A blood pressure monitor apparatus according to claim 1, further comprising an output device which outputs, in a two-dimensional coordinate plane, a trend graph including the estimated blood pressure values successively determined by the estimated blood pressure determining means, along a time axis of the coordinate plane.

* * * * *